United States Patent [19]
Deckner et al.

[11] Patent Number: 5,855,876
[45] Date of Patent: *Jan. 5, 1999

[54] MOISTURIZING LIPSTICK COMPOSITIONS

[75] Inventors: George Endel Deckner, Cincinnati, Ohio; Crystal Turner, Baltimore, Md.; Sharron Hunter, Detroit, Mich.; Kim Watts-McMillan, Owings Mills, Md.

[73] Assignee: The Procter & Gamble Company, Cincinnati, Ohio

[ * ] Notice: The term of this patent shall not extend beyond the expiration date of Pat. No. 5,593,662.

[21] Appl. No.: 801,509

[22] Filed: Dec. 19, 1996

Related U.S. Application Data

[63] Continuation of Ser. No. 274,113, Jul. 12, 1994, Pat. No. 5,593,662, which is a continuation of Ser. No. 947,874, Sep. 21, 1992, abandoned.

[51] Int. Cl.$^6$ .......................... A61K 7/027; A61K 7/025
[52] U.S. Cl. ...................... 424/64; 424/63; 424/DIG. 5
[58] Field of Search .................. 424/63, 64, 401, 424/DIG. 5

[56] References Cited

U.S. PATENT DOCUMENTS

| | | | |
|---|---|---|---|
| 3,890,358 | 6/1975 | Hutchison et al. | 260/410.6 |
| 4,767,625 | 8/1988 | Mitsuno et al. | 424/95 |
| 5,108,737 | 4/1992 | Dunphy et al. | 424/64 |
| 5,176,902 | 1/1993 | Castro et al. | 424/63 |
| 5,362,494 | 11/1994 | Zysman et al. | 424/401 |
| 5,437,859 | 8/1995 | Ser et al. | 424/59 |
| 5,539,129 | 7/1996 | Zysman et al. | 549/430 |

FOREIGN PATENT DOCUMENTS

| | | | |
|---|---|---|---|
| 0534823 B1 | 3/1993 | European Pat. Off. | A61K 7/00 |

*Primary Examiner*—Sally Gardner-Lane
*Attorney, Agent, or Firm*—George W. Allen; John M. Howell; David L. Suter

[57] ABSTRACT

The present invention is for long lasting, physically stable, moisturizing lipstick compositions essentially free of water. Said lipsticks contain lipophilic materials with high levels of moisturizers distributed throughout. Said lipsticks resist separation of the moisturizing material from the body of the lipstick.

1 Claim, No Drawings

MOISTURIZING LIPSTICK COMPOSITIONS

This is a continuation of a File Wrapper Continuation application Ser. No. 08/274,113, filed on Jul. 12, 1994, which will issue as U.S. Pat. No. 5,593,662, on Jan. 14, 1997; which is a File Wrapper Continuation of application Ser. No. 07/947,874. filed on Sep. 21, 1992, abandoned.

TECHNICAL FIELD

The present invention relates to moisturizing lipstick compositions essentially free of water. Said lipsticks are long lasting and provide excellent moisturizing benefits to the lips.

BACKGROUND OF THE INVENTION

Lipsticks have been used for many years to accentuate the positive aspects of the wearer's lips. Lipsticks are capable of altering the apparent facial characteristics of the wearer. For example, narrow lips may be widened and broad lips narrowed. Besides altering the shape of the lips, lipsticks can be made in a great number of colors and shades to promote a desired effect or express the mood of the wearer.

Waxy and oily based materials are included in lipsticks to give the lips a moist and alluring look. Lipsticks also often contain emollients which provide a supple and pleasant feeling to the lips of the wearer. It has been proposed in JPA 61/83110 (Konuki) that lipsticks which contain water in addition to waxes and oils are more effective in moisturizing the lips. Said water is emulsified in the waxy material by the use of dispersing agents such as cholesterol, phytosterol, phospholipids, and/or saponifins, anionic surfactants, cationic surfactants, nonionic surfactants or amphoteric surfactants. U.S. Pat. No. 5,085,856, issued Feb. 4, 1992 (Dunphy et al.), teaches that sticks made according to JPA 61/83110 are deficient in terms of storage stability. Dunphy discloses water containing lipsticks are in fact stable provided the sticks contain the proper types of emulsifiers. Despite the purported benefits of water-containing lipsticks, consummers still favor anhydrous lipsticks since these usually last much longer.

Anhydrous lipsticks are disclosed in the prior. The following patents are examples of such compositions:

U.S. Pat. No. 2,853,422, issued Sep. 23, 1958 (Jarrett) discloses anhydrous lipsticks containing water soluble dyes wherein said dyes are dispersed in a polar solvent such as propylene glycol and polyethylene glycol leci-oleate prior to their dispersion into the waxy and oily material as small droplets or veins.

U.S. Pat. No. 5,034,216, issued Jul. 23, 1991 (Baron et al.), discloses anhydrous, 3-phase powder-like cosmetic products such as lipsticks comprising ethylene/acrylate copolymers, a powder phase and an oil phase.

U.S. Pat. No. 5,034,217, issued Jul. 23, 1991 (DeFrossez et al.) discloses anhydrous cosmetic make-up compositions including lip rouges which contain cross-linked poly beta alanine microspheres impregnated with a polyhydric alcohol.

U.S. Pat. No. 5,039,518, issued Aug. 13, 1991 (Baron et al.), discloses cosmetic stick compositions such as lipsticks comprising PVP/hexydecene copolymer, esters, phenyl trimethicone, spherical silica, bismuth oxychloride, mica, and cosmetic waxes.

U.S. Pat. No. 5,080,889, issued Jan. 14, 1992 (Katada et al.), discloses mono- and diacetylglycerine compositions. Said compositions are siad to have superior spreadability, smoothness, low stickiness, and feeling of moisture.

U.S. Pat. No. 5,093,111, issued Mar. 3, 1992 (Baker et al.), discloses anhydrous lipstick compositions comprising waxes, oils, colorants, cetearyl isocyanate sequestearate, and isopropyl hydroxy stearate. The later two components act as plasticizers which effectively modify the hardness of the waxes providing smooth application and good pliability on the lips during wear.

U.S. Pat. No. 5,108,736, issued Apr. 28, 1992 (Slossman), discloses pigmented cosmetic products in cake, cream, liquid or stick form made with pigments which are dispersed by the method disclosed therein to avoid processing said pigments using water. Eliminating water is said to provide numerous advantages in processing and avoidance of microbiological contamination.

Co-pending patent application, Moister, Longer-Lasting Lipsticks, El-Nokaly et al., U.S. Ser. No. 07/947,692 filed Sep. 21, 1992 discloses anhydrous moisturizing lipstick compositions containing polymeric liquid crystals. The liquid crystals entrap moisturizers avoiding weeping. These lipstick compositions, therefore, have excellent stability and good moisturizing properties.

SUMMARY OF THE INVENTION

The present invention corresponds to long lasting, physically stable, moisturizing lipsticks essentially free of water. Said lipsticks comprise lipophilic materials as the continuous phase, and high levels of moisturizers. These sticks maximize lip moisturization while resisting separation of the moisturizer from the body of the lipstick.

More particularly the present invention provides a moisturizing lipstick composition essentially free of water comprising:

(a) from about 30% to about 80% lipophilic materials;

(b) from about 2% to about 20% moisturizer;

(c) from about 0% to about 35% of a colorant; and (d) from about 1% to about 20% of a coupling agent.

DETAILED DESCRIPTION OF THE INVENTION

The components utilized in the present invention are described in detail below. All percentages and ratios herein are by weight unless otherwise indicated.

LIPOPHILIC MATERIALS

In the present invention lipophilic materials comprise from about 30% to about 80%, preferably from about 40% to about 70%, and most preferably from about 50% to about 65% of the composition Said lipophilic materials include liquid and solid materials known in the art.

Liquids

Liquids comprise from about 20% to about 90%, preferably from about 30% to about 60% of the lipophilic material. By liquid, it is meant that the material freely flows at room temperature. Said liquids are selected from the group consisting of hydrocarbon oils, fatty acid esters, fatty alcohols, and mixtures thereof.

Hydrocarbon oils useful in the present invention are both natural and synthetically produced oils comprising saturated and unsaturated fatty acids. Saturated fatty acids found in the hydrocarbon oils of the present invention are selected from the group consisting of adipic, caprylic, capric, lauric, myristic, palmitic, stearic, and mixtures thereof. Unsaturated fatty acids found in the hydrocarbon oils of the present invention are selected from the group consisting of linoleic linolenic, ricinoleic, oleic, elaidic, erucic, and mixtures thereof. The hydrocarbon oils used herein typically are mixtures of the above fatty acids. Hydrocarbon oils derived from natural sources such as plants contain mixtures of the above mentioned fatty acids. These hydrocarbon oils include castor bean oil, or castor oil, rapeseed oil, soybean oil, palm kernel oil, babassu kernel oil, coconut oil, and mixtures thereof.

Hydrocarbon oils derived from mineral sources can also be used in the present invention. These hydrocarbon oils are generally derived from petroleum and include mineral oils, petrolatum, and mixtures thereof.

Fatty alcohols useful in the present invention are materials which contain a hydroxyl group attached to a fat chain. Such fatty alcohols are disclosed in Fukushima et al, "The Effect of Cetostearyl Alcohol in Cosmetic Emulsions", 98 Cosmetics & Toiletries 89–102 (1983). The fatty alcohols used herein are selected from the group consisting of cetearyl alcohol, cetyl alcohol, myristyl alcohol, stearyl alcohol, isostearyl alcohol, lanolin alcohol, lauryl alcohol, oleyl alcohol, stearyl alcohol, octyldodecanol alcohol, and mixtures thereof. Preferred are cetyl alcohol, oleyl alcohol, stearyl alcohol, and mixtures thereof.

The fatty acid esters useful in the present invention are fatty acids whose active hydrogen has been replaced by the alkyl (group of monohydric and polyhydric alcohols (the fatty acid esters of the polyhydric alcohol glycerol being triglycerides). In the present invention the fatty acid esters are selected from the group consisting of cetyl ricinoleate, cetyl acetate, glycerol oleate, glycerol monostearate, isopropyl lanolate, isopropyl linoleate, isopropyl myristate, isopropyl palmitate, isopropyl oleate, isopropyl stearate, ethyl glutimate, ethyl laurate, ethyl linolenate, ethyl methacrylate, ethyl myristate, ethyl palmitate, and mixtures thereof. The preferred fatty acid ester is selected from the group consisting of isopropyl myristate, isopropyl palmitate, isopropyl oleate, isostearate, and mixtures thereof.

In the present invention, a preferred hydrocarbon oil comprises:

a. from about 20% to about 40% castor oil;
 b. from about 5% to about 15% isopropyl palmitate;
 c. from about 2% to about 15% of $C_6$ to $C_{18}$ fatty acids;
 d. from about 0% to about 10% lanolin; and
 e. from about 0% to about 10% lanolin oil.

Solids

The lipophilic materials also contain from about 10% to about 80%, preferably from about 40% to about 70% solids. By solid it is meant that the material is firm and has a plastic texture at room temperature. Said solids are selected from the group consisting of fatty alcohols, fatty acid esters, waxes having melting points from about 55° C. to about 110° C., and mixtures thereof.

A general description of the fatty alcohols comprising the solid is disclosed above under liquids. However, in order to be a solid the carbon chain length is generally greater than 11. The fatty alcohols used herein are selected from the group consisting of saturated, unsaturated, and mixtures of saturated and unsaturated fatty acids. The saturated fatty alcohols are selected from the group consisting of octyl, decyl, myristyl, cetyl, stearyl alcohols and mixtures thereof. The unsaturated fatty alcohols are selected from the group consisting of oleyl, linoleyl, linolenyl, arachidyl fatty alcohols and mixtures thereof.

A general description of fatty acid esters comprising the solid is disclosed above under liquids. Solid fatty acid esters require a carbon chain length greater than 10. In the present invention, the solid in the lipophilic material is selected from the group consisting of saturated fatty acid esters, unsaturated fatty esters, and mixtures thereof. The fatty acid esters are selected from the group consisting of linoleic, linolenic, oleic, palmitoleic, caproleic fatty acid esters, and mixtures thereof.

Waxes are also useful as the solid in the present invention. The waxes-have melting points from about 55° C. to about 110° C. and typically are selected from the group consisting of $C_8$ to $C_{50}$ hydrocarbon waxes. The preferred waxes of the present invention are selected from the group consisting of candelilla, beeswax, carnauba, spermaceti, montan, ozokerite, ceresin, paraffin, modified beeswax, bayberry, castor waxes, synthetic waxes, microcrystalline waxes and mixtures thereof. More preferably the waxes are selected from the group consisting of candelilla, modified beeswax, carnauba, ozokerite, ceresin, paraffin, and mixtures thereof. Most preferably, the waxes are selected from the group consisting of candelilla, modified beeswax, ozokerite, carnauba, and mixtures thereof. A particularly preferred mixture of waxes used in the present invention is as follows:

a. from about 6.5% to about 8.5% candelilla wax;
 b. from about 2% to about 4.5% ozokerite wax;
 c. from about 0.1% to about 1 carnauba wax; and
 d. from about 3% to about 5% modified beeswax.

MOISTURIZERS

The lipstick of the present invention comprises from about 2% to about 20%, preferably from about 8% to about 15%, and most preferably from about 10% to about 13% of a moisturizer. The moisturizers are dispersed in the lipophilic or continuous phase of the anhydrous lipstick of the present invention. Said moisturizers are hydrophilic and comprise polyhydric alcohols, ethoxylated and propoxylated polyols, polysacharides, and mixtures thereof. Preferred moisturizers are selected from the group consisting of glycerine, panthenol, hexylene glycol, polyethylene glycol, polypropylene glycol, sorbitol, and mixtures thereof. Most preferred is glycerine.

COLORANTS

Lipsticks of the present invention contain from about 0% to about 35%, preferably from about 0.5% to about 30%, and most preferably from about 5% to about 15% by weight of a colorant. Colorants useful in the present invention are FD&C approved dyes, pigments, and mixtures thereof.

Colorants useful in the present invention are disclosed in U.S. Pat. No. 4,996,044, issued Feb. 26, 1991, herein incorporated by reference. The dyes and pigments useful in the present invention are selected from the group consisting of lake dyes, micas or pearls, iron oxides, titanium oxides calcium carbonates, treated pigments, and mixtures thereof. Preferred for use herein are laked dyes. Laked dyes are are organic pigments produced by the interaction of an oil-soluble organic dye, a precipitant, and an absorptive inorganic substrate.

The colorants are typically dispersed in an oily medium prior to addition to the present composition. Colorants can be bought already dispersed in an oily medium like castor oil, or as dry powders which subsequently are dispersed in a chosen medium by the formulator. Such colorants are available from H. Kohnstamn and Company.

COUPLING AGENT

In the present invention coupling agents are used at a level from about 2% to about 20%, preferably from about about 3% to about 15%, most preferably from about 5% to about 10%. The coupling agent is a polar material which has an affinity for the lipophilic material, but also has an affinity for the hydrophilic moisturizers used in the present invention. Therefore, the coupling agent facilitates the retention of the moisturizers in the lipophilic material of the lipstick. The coupling agents useful in the present invention are selected from the group consisting of glyceryl esters of fatty acid esters, phospholipids, glyceryl monoalkanoates, glyceryl monoalkenoates, sucrose esters, sorbitan fatty alcohol mono esters, polyglyceryl esters, modified beeswax, and mixtures thereof. These coupling agents are disclosed in U.S. Pat. No. 5,085,856, issued Feb. 4, 1992, and U.S. Pat. No. 4,948,584, issued Aug. 14, 1990; both herein incorporated by reference.

The coupling agents used in the present invention are selected from the group consisting of glyceryl monostearate, a 3:1 to 1:3 mixture of propylene glycol/glyceryl oleate, cetyl alcohol, lecithin, modified beeswax, and mixtures thereof.

Lecithin is a naturally derived product from soybeans and is a naturally occuring mixture of diglycerides and stearic, palmitic, and oleic fatty acids linked to the choline ester of phosphoric acid. Modified beeswax is treated to remove free acids present in natural beeswax. This wax is ideal for cosmetic use since it does not cause any crystalization in the fatty phase. Modified beeswax also has sufficient lipophilic properties and, therefore, is useful as one of the waxes disclosed in the solid lipophilic material above. Such waxes include Polyglycerol-3 Beeswax wherein the free fatty acids in beeswax, often responsible for granular characteristics have been removed. Such wax is available as Cera Bellina™ from Koster Keunen.

ADDITIONAL INGREDIENTS

The lipstick composition of the present invention can contain additional ingredients known in the art for use in cosmetic compositions.

Among the additional ingredients that can be used in the present invention are stabilizers, preservatives, skin conditioning agents, wear extending agents, and vitamins. Skin conditioning agents are well known in the art, and are summarized in The CTFA Cosmetic Ingredient Handbook, pages 79–85, 1st Edition, 1988 incorporated herein by reference. Said skin conditioning agents include emollients, humectants, occlusives, and skin protectants. Examples of skin conditioning agents include zinc oxide, beta-glyceyrrhetic acid, chamomoile oil, ginko bilova extract, pyroglutamic acid salts or esters, sodium hylauronate, 2-hydroxyoctanoic acid, sulfur, salacylic acid, carboyxmethyl cysteine, panthenol, vitimins A and E, lanolin, cholesterol, and mixtures thereof.

EXAMPLES

Example 1

| INGREDIENT | W/W % |
|---|---|
| Lipophilic Material | |
| Castor Oil | 3.10 |
| Polybutene | 0.64 |
| Isopropyl Palmitate | 9.28 |
| Caprylic/Capric/Isostearic/Adipic Triglycerides | 2.02 |
| Candelilla Wax | 7.59 |
| Medium Chain Triglyceride Oil[1] | 1.66 |
| Cetyl Ricinoleate | 10.50 |
| Modified Beeswax [2] | 3.26 |
| Ozokerite | 2.88 |
| Lanolin Oil | 2.00 |
| Carnauba Wax | 0.46 |
| Glycerine | 12.50 |
| Panthenol | 5.00 |
| Glyceryl Monostearate | 2.77 |
| Propylene Glycol/Glyceryl Oleate (1:1 ratio) | 4.70 |
| Lecithin [3] | 1.03 |
| Ascorbyl Palmitate | 0.50 |
| Propylparaben | 0.10 |
| Colorant[4] | 30.00 |
| Total | 100.00 |

[1] MCT Oil available from Mead Johnson Co., Evansville Ind.
[2] Cera Bellina Beeswax available from Koster-Keunen.
[3] Centrolex F available from American Soya.
[4] FD&C colorants available from H. Kohnstamn and Company.

Examples 2, 3, and 4

| INGREDIENT | Example 2 | Example 3 | Example 4 |
|---|---|---|---|
| Lipophilic Material | | | |
| Modified Beeswax [1] | 4.82 | 3.71 | 3.71 |
| Candelilla Wax | 7.76 | 8.58 | 7.85 |
| Caprylic/Capric/Isostearic/Adipic Triglycerides | 8.21 | 6.34 | 6.35 |
| Carnauba Wax | 0.47 | 0.52 | 0.48 |
| Castor Oil | 22.93 | 17.63 | 19.87 |
| Cetyl Ricinoleate | 0.00 | 11.87 | 11.89 |
| Cholesterol Hydroxystearate | 0.00 | 0.00 | 0.00 |
| Isopropyl Palmitate | 13.64 | 10.49 | 10.51 |
| Lanolin | 8.23 | 0.00 | 0.00 |
| Lanolin Oil | 2.94 | 2.26 | 2.26 |
| Medium Chain Triglyceride Oil [2] | 6.82 | 5.24 | 5.25 |
| Ozokerite | 2.95 | 3.26 | 2.98 |
| Petrolatum | 0.00 | 0.00 | 0.00 |
| Polybutene | 0.94 | 0.72 | 0.72 |
| Glycerin | 5.65 | 14.13 | 14.15 |
| Glyceryl Monostearate | 4.12 | 3.13 | 0.00 |
| Glyceryl Oleate/Propylene Glycol (1:1 ratio) | 7.08 | 5.31 | 7.13 |
| Lecithin [3] | 1.18 | 1.16 | 1.19 |
| Panthenol | 2.26 | 5.65 | 5.66 |
| TOTAL | 100.00 | 100.00 | 100.00 |

[1] Cera Bellina Beeswax available from Koster-Keunen.
[2] MCT Oil available from Mead Johnson Co., Evansville Ind.
[3] Centrolex F available from American Soya.

Examples 5, 6, and 7

| INGREDIENT | Example 5 | Example 6 | Example 7 |
|---|---|---|---|
| Lipophilic Material | | | |
| Candelilla Wax | 5.94 | 6.93 | 6.93 |
| Caprylic/Capric/Isostearic/Adipic Triglycerides | 3.13 | 7.35 | 7.00 |
| Carnauba Wax | 0.36 | 0.42 | 0.42 |
| Castor Oil | 0.00 | 20.48 | 20.48 |
| Modified Beeswax [1] | 3.69 | 4.31 | 4.31 |
| Cetyl Ricinoleate | 0.00 | 8.50 | 0.00 |
| Cholesterol Hydroxystearate | 0.00 | 6.09 | 0.00 |
| Isopropyl Palmitate | 10.44 | 12.16 | 12.18 |
| Lanolin (Acteylated) | 6.30 | 0.00 | 2.63 |

-continued

| INGREDIENT | Example 5 | Example 6 | Example 7 |
|---|---|---|---|
| Lanolin Oil | 2.25 | 2.63 | 0.00 |
| Medium Chain Triglyceride Oil [2] | 2.60 | 0.00 | 5.80 |
| Ozokerite | 2.25 | 2.63 | 2.63 |
| Petrolatum | 0.00 | 0.00 | 10.50 |
| Polybutene | 0.72 | 0.84 | 0.84 |
| Glycerin | 12.50 | 8.50 | 7.00 |
| Glyceryl Monostearate | 3.15 | 0.00 | 0.00 |
| Glyceryl Oleate/ Propylene Glycol (1:1) | 5.40 | 6.30 | 6.30 |
| Lecithin [3] | 0.90 | 1.05 | 1.05 |
| Panthenol | 5.00 | 2.00 | 2.00 |
| Ascorbyl Palmitate | 0.50 | 0.50 | 0.50 |
| Propylparaben | 0.10 | 0.10 | 0.10 |
| Colorant [4] | 34.77 | 9.19 | 9.33 |
| TOTAL | 100.00 | 100.00 | 100.00 |

[1.] Cera Bellina Beeswax available from Koster Keunen.
[2.] MCT Oil available from Mead Johnson Co., Evansville Ind.
[3.] Centrolex F available from American Soya.
[4.] FD&C colorants available from H. Kohnstamn and Company.

Examples 8 and 9

| INGREDIENT | Example 8 | Example 9 |
|---|---|---|
| Lipophilic Material | | |
| Candelilla Wax | 7.59 | 7.59 |
| Caprylic/Capric/Isostearic/ Adipic Triglycerides | 4.60 | 2.01 |
| Carnauba Wax | 0.46 | 0.46 |
| Castor Oil | 17.55 | 0.00 |
| Modified Beeswax [1] | 3.28 | 3.28 |
| Cetyl Ricinoleate | 10.50 | 10.50 |
| Cholesterol Hydroxystearate | 0.00 | 0.00 |
| Isopropyl Palmitate | 9.28 | 9.28 |
| Lanolin (Acetylated) | 0.00 | 0.00 |
| Lanolin Oil | 2.00 | 2.00 |
| Medium Chain Triglyceride Oil [2] | 3.64 | 1.66 |
| Ozokerite | 2.88 | 2.88 |
| Petrolatum | 0.00 | 0.00 |
| Polybutene | 0.64 | 0.64 |
| Glycerin | 12.50 | 12.50 |
| Glyceryl Monostearate | 2.77 | 2.77 |
| Glyceryl Oleate/ Propylene Glycol (1:1) | 4.70 | 4.70 |
| Lecithin [3] | 1.03 | 1.03 |
| Panthenol | 5.00 | 5.00 |
| Ascorbyl Palmitate | 0.00 | 0.50 |
| Propylparaben | 0.10 | 0.10 |
| 3-Pentadecyl Phenyl Ether [4] | 1.50 | 0.00 |
| Colorants [5] | 9.98 | 33.10 |
| TOTAL | 100.00 | 100.00 |

[1.] Cera Bellina Beeswax available from Koster Keunen.
[2.] MCT Oil available from Mead Johnson Co., Evansville Ind.
[3.] Centrolex F available from American Soya.
[4.] Pentadoxynol-200 available from RTD Chemicals Corp.
[5.] FD&C colorants available from H. Kohnstamn and Company.

Lipstick compositions of the present examples are made in the following way:

Combine the lipophilic materials in a vessel equiped for heating and mixing. Heat the mixture to a temperature between 85°–95° C., mixing until a homogeneous melt forms. Cool the melt until it solidifies. Combine the polar solvent and dispersing agent in a separate vessel equiped for heating and mixing. Heat the mixture to a temperature between 75°–85° C. until a melt is formed. Homogenize the said melt and add it to the vessel containing the solidified lipophilic material. Heat the mixture to between 85°–95° C., mixing until a homogeneous melt forms. Cool the mixture until it solidifies. Mix the colorant slurry until it is homogeneous and add it to the vessel containing the solidified mixture above. Heat the mixture to between 75°–85° C., mixing until a homogeneous melt is formed. Pour the mixture into lipstick molds and remove when the mixture has solidified.

What is claimed is:

1. An anhydrous moisturizing lipstick which is essentially free of water and which comprises:

A. from about 30% to about 80% lipophilic material with from about 20% to about 90% of said lipophilic material comprising liquids selected from the group consisting of:
   a) a hydrocarbon oil component which comprises:
      i) from about 20% to about 40% of the composition of castor oil;
      ii) from about 5% to about 15% of the composition of isopropyl palmitate;
      iii) from about 2% to about 15% of the composition of $C_6$ to $C_{18}$ fatty acids;
      iv) from about 0% to about 10% of the composition of lanolin; and
      v) from about 0% to about 10% of the composition of lanolin oil;
   b) fatty acid esters;
   c) fatty alcohols; and
   d) mixtures of said liquids; and with from about 10% to about 80% of said lipophilic material comprising solids selected from the-group consisting of
   a) fatty alcohols;
   b) fatty acid esters;
   c) a wax component which comprises:
      i) from about 6.5% to about 8.5% of the composition of candelilla wax;
      ii) from about 2% to about 4.5% of the composition of ozokerite wax;
      iii) from about 0.1% to about 1% of the composition of carnauba wax; and
      iv) from about 3% to about 5% of the composition of beeswax having the free fatty acids removed therefrom; and
   d) mixtures of said solids;

B. from about 2% to about 20% hydrophilic moisturizer which is dispersed in the lipophilic material and which is selected from the group consisting of polyhydric alcohols, ethoxylated polyols, propoxylated polyols, polysaccharides and mixtures thereof;

C. from about 5% to about 35% of a colorant;

D. from about 2% to about 20% of a coupling agent selected from the group consisting of glyceryl esters of fatty acid esters, phospholipids, glyceryl monoalkanoates, glyceryl monoalkenoates, sucrose esters, sorbitan fatty alcohol mono esters, polyglyceryl esters, and mixtures thereof; and E. other ingredients selected from the group consisting of skin conditioning agents, stabilizers, preservatives and mixtures thereof.

* * * * *